United States Patent [19]

Ruckes et al.

[11] Patent Number: 4,851,567

[45] Date of Patent: Jul. 25, 1989

[54] N,N'-BIS(5-ISOCYANATONAPHTHYL-)UREA, A PROCESS FOR ITS PRODUCTION, AND ITS USE

[75] Inventors: Andreas Ruckes; Gerhard Grögler, both of Leverkusen; Richard Kopp, Cologne; Heinrich Hess, Leverkusen, all of Fed. Rep. of Germany

[73] Assignee: Bayer Aktiengesellschaft, Leverkusen, Fed. Rep. of Germany

[21] Appl. No.: 295,636

[22] Filed: Jan. 10, 1989

[30] Foreign Application Priority Data

Jan. 16, 1988 [DE] Fed. Rep. of Germany ....... 3801091

[51] Int. Cl.$^4$ ............................................. C07C 69/00
[52] U.S. Cl. ................................................... 560/330
[58] Field of Search ................................. 560/330, 359

[56] References Cited

U.S. PATENT DOCUMENTS 2,757,185 7/1966 Barthel ................................ 260/453

FOREIGN PATENT DOCUMENTS 543890 7/1957 Canada ................................ 560/359

*Primary Examiner*—Alan Siegel
*Attorney, Agent, or Firm*—Gene Harsh; Joseph C. Gil; Richard E. L. Henderson

[57] ABSTRACT

This invention relates to N,N'-bis(5-isocyanatonaphthyl)urea and a process for its preparation by hydrolysis of naphthalene-1,5-diisocyanate. This invention also relates to a method for preparing a polyurethane or polyurea comprising reacting N,N'-bis(5-isocyanatonaphthyl)urea with an NCO-reactive compound.

4 Claims, No Drawings

N,N'-BIS(5-ISOCYANATONAPHTHYL)UREA, A PROCESS FOR ITS PRODUCTION, AND ITS USE

BACKGROUND OF THE INVENTION

The present invention relates to N,N'-bis (5-isocyanatonaphthyl)urea obtainable by reaction of naphthalene-1,5-diisocyanate ("NDI") and water in an inert solvent. The urea according to the invention, which may optionally contain a small amount of oligomeric ureas, may be used with advantage in the synthesis of polyurethane or polyurea elastomers.

It is known that monoisocyanates react with water to form N-substituted carbamic acid derivatives which can be converted into urea derivatives by reaction with more isocyanate in a reaction accompanied by elimination of carbon dioxide. Polyureas are similarly obtained from diisocyanates and water by polyaddition.

It is also known that, provided certain reaction conditions are maintained, it is possible to obtain a low molecular weight urea diisocyanate corresponding to the following general formula

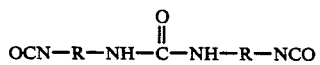

by allowing 1 mol of water to react with at least 2 mol of a diisocyanate in a solvent at temperatures of from 0° C. to 30° C. As described in DAS No. 1,101,394, this reaction can only be carried out with diisocyanates which, like 2,4-tolylene diisocyanate, for example, contain isocyanate groups of different reactivities.

According to U.S. Pat. No. 2,757,185, compounds such as meta- or para-phenylene diisocyanate form only polymeric and not monomeric ureas when reacted with water.

It has now surprisingly been found that N,N'-bis(5-isocyanatonaphthyl)urea, which optionally contains only a small amount of oligomeric ureas, can be obtained in a high yield by reaction of naphthalene diisocyanate with water in a molar ratio of about 2:1 in inert solvents at a concentration of at least 2% by weight, based on the solvent used. A basic catalyst may optionally be used.

The urea according to the invention may be advantageously used for the production of polyurethane or polyurea elastomers.

In comparison with elastomers based on NDI, elastomers obtained using the urea according to the invention are characterized not only by excellent mechanical properties, but also especially by high thermal stability. By virtue of its high melting point, the urea according to the invention is also suitable as a heterogeneous isocyanate component in one-component systems according to DE-OS No. 3,230,757. Another advantage is that sublimation, which is a troublesome tendency when processing NDI in the melt, does not occur where the corresponding urea is used, thereby providing simple and safe handling.

SUMMARY OF THE INVENTION

The present invention relates to N,N'-bis (5-isocyanatonaphthyl)urea of Formula I.

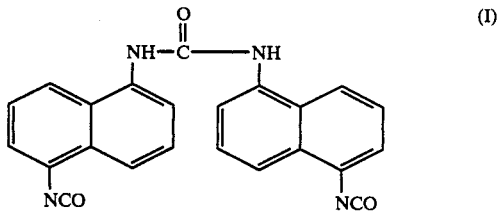

The invention also relates to compositions consisting essentially of the compound of Formula I, optionally containing a small amount of oligomeric urea, obtainable from the reaction of naphthalene-1,5-diisocyanate and water under the conditions described in detail below. The invention further relates to reacting the compound of Formula I with an NCO-reactive compound to form polyurethanes or polyureas.

DESCRIPTION OF THE INVENTION

The starting component for the process according to the invention is, for example, the naphthalene-1,5-diisocyanate obtainable from Bayer AG under the trade name Desmodur®15.

Suitable solvents are those in which the NDI and at least part of the water required are soluble. In addition, suitable solvents should not contain any NCO-reactive groups; that is, such solvents must be essentially inert or non-reactive to isocyanates. Suitable solvents include ethers, such as dioxane or diisopropyl ether; ketones, such as acetone or methyl ethyl ketone; and esters, such as isopropyl acetate or cellosolve acetate. The entire required quantity of water need not be completely dissolved in the solvent used. However, solvents such as halogenated hydrocarbons, in which water is substantially insoluble, are unsuitable as solvents according to the invention. Preferred solvents are dioxane and diisopropyl ether.

The concentration of the naphthalene diisocyanate in the solvent is generally not critical. In cases of excessive dilution, however, the urea obtained may have a greatly reduced NCO content. A concentration of >2% by weight NDI, based on the solvent, is preferably maintained.

The quantity of water substantially corresponds to the quantity theoretically required for reaction with two isocyanate groups to form a urea group, or about one mol of water for each two mols of naphthalene-1,5-diisocyanate. If insufficient water is used, unreacted starting isocyanate remains behind and must be separated. On the other hand, if too much water is used, the polyurea obtained has a greatly reduced NCO content.

The urea formed is substantially insoluble in the solvents mentioned above and is thus no longer accessible to any further reaction of the NCO groups still present. Thus, of the NDI used, only one NCO group per molecule generally takes part in formation of the urea groups.

To obtain better volume-time yields, higher reaction temperatures (preferably room temperature −110° C.) and/or a catalyst may be used to accelerate the reaction between water and NDI. Preferred catalysts are the catalysts normally used in polyurethane chemistry, such as, for example, tertiary amines (e.g., N,N-dimethylbenzylamine) or organometallic compounds (e.g., tin(II) dioctoate or dibutyl tin diacetate).

Upon completion of the reaction, the precipitating product is filtered off under suction through a suitable filter, washed with an inert solvent (such as, for example, petroleum ether), and dried in a drying cabinet (preferably in vacuo) at low temperatures.

The NCO content of the product obtained by this process is normally only slightly below the calculated NCO content. To obtain satisfactory volume-time yields, however, the reaction conditions generally must be selected in such a way that the urea compositions obtained, due to slight oligourea formation, show a lower NCO content than the theoretical content. This choice must often be made because it has been found that measures that increase the reaction velocity (such as increased temperature and use of polar water-soluble solvents) and thus produce an increase in the yield in a reduced reaction time, always also bring about a reduction in the NCO content of the urea composition. However, such products may be used as long as the oligourea formation does not exceed certain limits.

The storable and easily handled urea composition of the invention accumulates as a finely divided crystalline powder, which, dependent on the reaction conditions, has an NCO content of at least 15% by weight and preferably of at least 19% by weight.

The urea according to the invention may be used advantageously in its low molecular weight or "low-oligomer" form for the synthesis of polyurethane systems. In general, the urea is first finely ground (for example, in a ball mill) until it has an average particle size of 1 to 50 $\mu$m (preferably 3 to 10 $\mu$m).

The urea according to the invention is preferably used for the production of cast elastomers, in which polyester polyols or polyesters terminated by aromatic amino groups are used as NCO-reactive components. The polyester polyamines are preferably obtained in accordance with EP-AS Nos. 0,219,035 by hydrolysis of isocyanate-terminated compounds. In this process, polyesters containing preferably 2 or 3 hydroxyl groups are converted to NCO prepolymers and, in a second step, the isocyanate groups are converted into an amino group by hydrolysis. Elastomers having outstanding thermal stability and excellent mechanical properties are obtained.

The following examples illustrate the preparation of the urea according to the invention and its use in the production of high-quality polyurethane elastomers. The present invention, which is set forth in the foregoing disclosure, is not to be construed or limited either in spirit or in scope by these examples. The naphthalene-1,5-diisocyanate used in the examples is the product obtainable from Bayer AG as Desmodur ®15.

DESCRIPTION OF THE PREFERRED EMBODIMENTS

EXAMPLE 1

Preparation of the urea according to the invention

Naphthalene-1,5-diisocyanate (287 g, 1.36 mol) is dissolved in 4 l of dioxane. After addition of 12.5 ml (0.69 mol) water, the reaction mixture is stirred for 20 h at room temperature. The precipitated product is filtered off, washed with the dioxane, and dried in a vacuum drying cabinet, yielding 52 g of a product urea diisocyanate having an NCO content of 20.0% by weight. After standing for a total of 6 days at room temperature, the filtrate yields another 122 g of product having an NCO content of 21.0% by weight. The NDI urea is obtained in a total yield of 65% (based on the diisocyanate compound used), with an average NCO content of 20.7% by weight (theoretical: 21.3% by weight).

EXAMPLE 2

Production of a cast elastomer using a polyester

A linear polyester of adipic acid and ethylene glycol (MW: 2000; OH value: 56 mg KOH/g) (200 g) is briefly dehydrated in a water jet vacuum at 80 to 100° C. After cooling to 50–60° C., 0.3 g lead octoate is added to the melt. The urea diisocyanate prepared according to Example 1 (NCO content 20.7% by weight) (48.6 g) in the form of a finely ground powder (particle size: 10–50 $\mu$m) is then stirred in using a suitable stirrer. No reaction between the polyester and the urea diisocyanate occurs at the temperature of 50–60° C. After brief degassing, the liquid reaction mixture can be poured into a preheated mold coated with a release agent and then heated for 3–4 h to 140–150° C. A highly elastic molding having the mechanical properties shown in Table 1 is obtained.

EXAMPLE 3

Production of a cast elastomer using a polyester amine

A polyester amine obtained in accordance with EP-AS No. 0,219,035 by basic hydrolysis of an NC prepolymer formed from 1 mol of the polyester used in Example 2 and 2 mol 2,4-diisocyanatotoluene (NH value 44.3 mg KOH/g) is used in this Example. NDI urea diisocyanate (38.5 g) is stirred into the melt of the polyester amine in the same way as in Example 1. The use of lead octoate is not necessary. After degassing, the reaction mixture is poured into a mold and then heated for 3–4 h to 140–150° C. Like the polyurethane elastomer described in Example 2, the resultant high-quality polyurethane elastomer shows surprisingly high thermal stability. Mechanical properties are shown in Table 1.

Table 1

Mechanical properties of the cast elastomers obtained in accordance with Examples 2 and 3

|  | Example 1 | Example 2 |
|---|---|---|
| Tensile strength (DIN 53504) | 21.0 MPa | 29.5 MPa |
| Breaking elongation (DIN 53504) | 700% | 550% |
| Tear Propagation resistance (DIN 53515) | 65 KN/m | 97KN/m |
| Shore A hardness (DIN 53505) | 94 | 97 |
| Elasticity (DIN 53512) | 48% | 45% |

What is claimed is:

1. N,N'-bis(5-isocyanatonaphthyl)urea.

2. A composition prepared by the process comprising hydrolyzing naphthalene-1,5-diisocyanate with about one mol of water for each two mols of naphthalene-1,5-diisocyanate in an essentially inert solvent.

3. A composition according to claim 2 wherein the concentration of naphthalene-1,5-diisocyanate is at least 2% by weight, based on the amount of solvent.

4. A composition according to claim 2 wherein the solvent is dioxane or diisopropyl ether.

* * * * *